United States Patent
Umlauf et al.

(10) Patent No.: US 9,880,178 B2
(45) Date of Patent: Jan. 30, 2018

(54) METHOD FOR AIDING DIAGNOSIS OF ALZHEIMER'S DISEASE

(71) Applicant: Randox Laboratories Ltd., Northern Ireland (GB)

(72) Inventors: Ellen Umlauf, Vienna (AT); Maria Zellner, Vienna (AT)

(73) Assignee: RANDOX LABORATORIES LTD., Crumlin (IE)

( * ) Notice: Subject to any disclaimer, the term of this patent is extended or adjusted under 35 U.S.C. 154(b) by 0 days.

(21) Appl. No.: 14/431,557

(22) PCT Filed: Oct. 3, 2013

(86) PCT No.: PCT/GB2013/052583
§ 371 (c)(1),
(2) Date: Mar. 26, 2015

(87) PCT Pub. No.: WO2014/053845
PCT Pub. Date: Apr. 10, 2014

(65) Prior Publication Data
US 2015/0247870 A1    Sep. 3, 2015

(30) Foreign Application Priority Data
Oct. 3, 2012 (GB) .................................. 1217688.9

(51) Int. Cl.
| | |
|---|---|
| *G01N 33/53* | (2006.01) |
| *G01N 33/567* | (2006.01) |
| *G01N 33/68* | (2006.01) |
| *G06F 19/18* | (2011.01) |
| *G06F 19/00* | (2011.01) |

(52) U.S. Cl.
CPC ......... *G01N 33/6896* (2013.01); *G06F 19/18* (2013.01); *G06F 19/345* (2013.01); *G01N 2333/4712* (2013.01); *G01N 2333/775* (2013.01); *G01N 2333/90* (2013.01); *G01N 2333/90638* (2013.01); *G01N 2333/91085* (2013.01); *G01N 2800/2821* (2013.01)

(58) Field of Classification Search
None
See application file for complete search history.

(56) References Cited

FOREIGN PATENT DOCUMENTS

| | | |
|---|---|---|
| WO | 2006/134390 A2 | 12/2006 |
| WO | 2011/067610 A1 | 6/2011 |

OTHER PUBLICATIONS

Hohwy, Morten, International Search Report, European Property Office, PCT/GB2013/052583, dated Dec. 11, 2013.
Ratcliffe, D90: Development of highly specific monoclonal antibodies to tropomyosin exons 1a and 9d for the development of a diagnostic blood test for Alzheimer's disease, Clinical Chemistry, 58(10): supplement; p. A174, Jul. 18, 2012.
Schevzov et al., "Tissue-specific Tropomyosin Isoform Composition," J. of HistoChem. & Cytochem., 53 (5):557-570, May 1, 2005.

*Primary Examiner* — Olga N Chernyshev
(74) *Attorney, Agent, or Firm* — Gavrilovich, Dodd & Lindsey LLP

(57) ABSTRACT

The present invention provides an ex vivo method for aiding the diagnosis of Alzheimer's disease in a patient comprising: (i) determining the number of alleles of ApoE4 in the patient's genome; (ii) determining the combined expression level of at least three platelet proteins in a platelet sample from the patient; and (iii) comparing the resulting value of step (ii) to a control value, wherein the at least three platelet proteins include at least one isoform of alpha-tropomyosin containing exon 1a and at least two platelet proteins selected from monoamine oxidase-B, coagulation factor XIIIa, wild-type GSTO-1 or mutant GSTO-1, wherein a result higher than the control value is indicative of Alzheimer's disease. The invention also provides a solid support comprising one or more ligands of at least one isoform of alpha-tropomyosin containing exon 1a, and one or more ligands of at least two platelet proteins selected from monoamine oxidase-B, coagulation factor XIIIa, wild-type GSTO-1 protein and/or mutant GSTO-1 protein immobilized thereon.

7 Claims, 8 Drawing Sheets

METHOD FOR AIDING DIAGNOSIS OF
ALZHEIMER'S DISEASE

CROSS REFERENCE TO RELATED APPLICATIONS

This application is a U.S. National Stage Application filed under 35 U.S.C. §371 and claims priority to International Application No. PCT/GB2013/052583, filed Oct. 3, 2013, which application claims priority to Great Britain Application No. GB 1217688.9, filed Oct. 3, 2012, the disclosure of which are incorporated herein by reference.

FIELD OF INVENTION

This invention relates to an ex vivo diagnostic method using the quantification of peripheral biomarkers of Alzheimer's disease.

BACKGROUND OF THE INVENTION

Late-onset Alzheimer's disease (LOAD) is a multifactorial disease characterised by neurofibrillary tangles and amyloid plaques and can only be definitely diagnosed post-mortem. The disease can begin many years before it is eventually diagnosed. In the early stages, short-term memory loss is the most common symptom. Later, symptoms include confusion, anger, mood swings, language breakdown, long-term memory loss, and the general decline of senses and bodily functions.

Alzheimer's disease (AD) is usually diagnosed clinically from the patient history, observations of relatives, and clinical observations. However, the presence of Alzheimer's disease-characteristic neurological and neuropsychological features such as amyloid plaques and neurofibrillary tangles can often only be determined post-mortem.

Most cases of Alzheimer's disease do not exhibit familial inheritance, however at least 80% of sporadic Alzheimer's cases involve genetic risk factors. Inheritance of the ε4 allele of the apolipoprotein E (ApoE) gene is regarded as a risk factor for development in up to 50% of late-onset sporadic Alzheimer's cases.

Diagnostic markers for neurological disorders are especially important in diagnosis early in the course of disease, when therapeutic compounds have the greatest potential effect. However, accurate diagnosis is difficult. Few diagnostic markers for early stage neuronal disorders are available and those that are available rely on the analysis of sample material (e.g. cerebrospinal fluid), which is difficult and painful to obtain. The use of protein biomarkers in diagnostic medicine is increasing. Identification of protein biomarkers of Alzheimer's disease, especially those present in readily accessible biological fluids such as blood and urine, represents a desirable and effective alternative to current diagnostic methods.

WO2011/067610 describes a method for aiding the diagnosis of Alzheimer's disease comprising determining the level of expression of at least four platelet proteins in a patient sample, wherein the number of alleles of ApoE4 determines the identity of the at least four platelet proteins selected.

However, there is a need to develop further diagnostic methods using peripheral biomarkers of Alzheimer's disease which enable simpler and more accurate diagnosis of disease.

SUMMARY OF THE INVENTION

According to a first aspect, the present invention provides an ex vivo method for aiding the diagnosis of Alzheimer's disease in a patient comprising: (i) determining the number of alleles of ApoE4 in the patient's genome; (ii) determining the combined expression level of at least three platelet proteins in a platelet sample from the patient; and (iii) comparing the resulting value of step (ii) to a control value, wherein the at least three platelet proteins include at least one isoform of alpha-tropomyosin containing exon 1a and at least two platelet proteins selected from monoamine oxidase-B, coagulation factor XIIIa, wild-type GSTO-1 or mutant GSTO-1, wherein a result higher than the control value is indicative of Alzheimer's disease.

According to a second aspect, the present invention provides a solid support comprising one or more ligands of at least one isoform of alpha-tropomyosin containing exon 1a, and one or more ligands of at least two platelet proteins selected from monoamine oxidase-B, coagulation factor XIIIa, alpha-tropomyosin containing exon 1a, wild-type GSTO-1 protein and/or mutant GSTO-1 protein immobilised thereon.

DESCRIPTION OF THE DRAWINGS

FIG. 6 shows 2D-Western Blot evaluation of tropomyosin exon 1a;

DETAILED DESCRIPTION OF THE INVENTION

Figure 1:
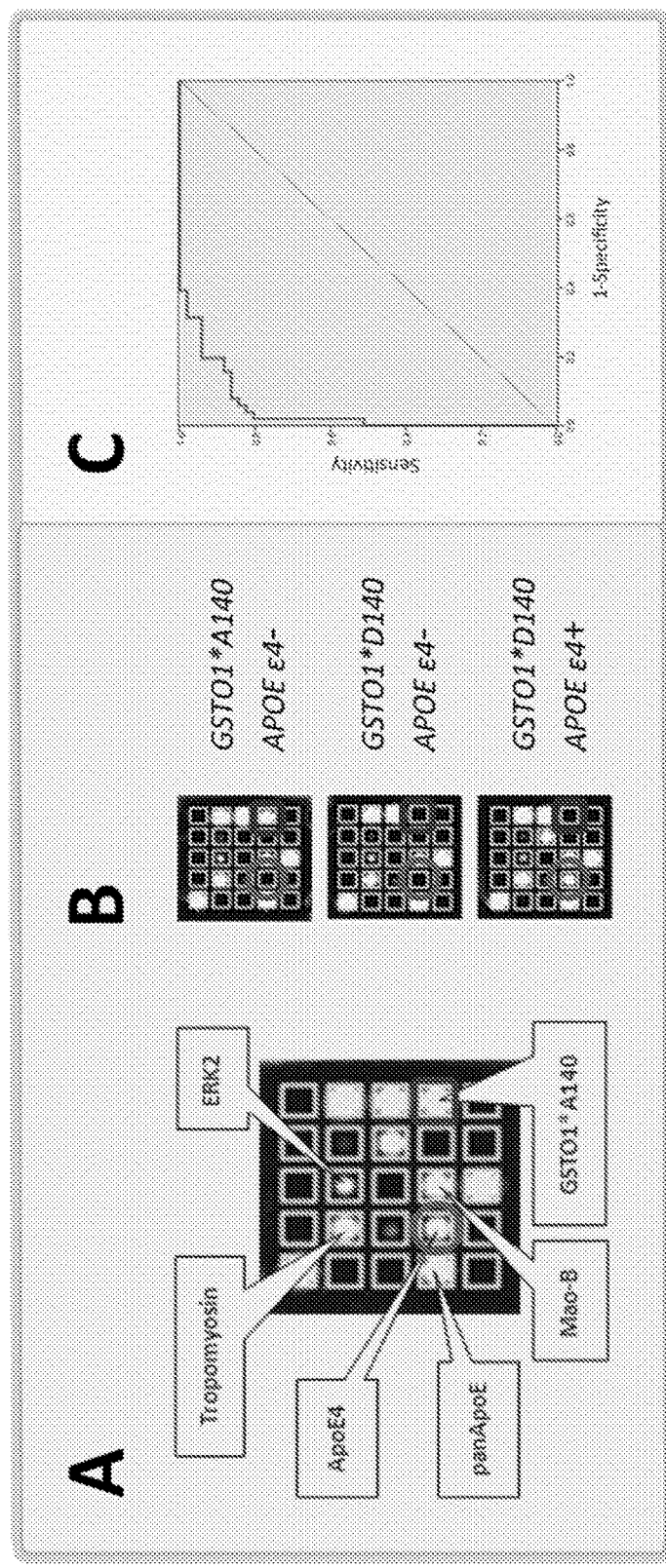
FIG. 1 shows a schematic representation of the new AD multiplex-protein biochip.

The present invention is based on the surprising finding that algorithm models containing a combination of at least three Late-onset Alzheimer's disease (LOAD) biomarkers selected from at least the group comprising monoamine oxidase B (MAO-B), glutathione S-transferase omega-1 wild type (wtGSTO-1) and mutant (mutGSTO-1), and certain isoforms of tropomyosin, can be used as a fast, easy, accurate, and cost-effective diagnostic tool for Alzheimer's disease using platelets that are easily isolated from whole blood.

According to a first aspect, the present invention provides an ex vivo method for aiding the diagnosis of Alzheimer's disease in a patient comprising: (i) determining the number of alleles of ApoE4 in the patient's genome; (ii) determining the combined expression level of at least three platelet proteins in a platelet sample from the patient; and (iii) comparing the resulting value of step (ii) to a control value, wherein a result higher than the control value is indicative of Alzheimer's disease. The method of the invention can be used to aid the diagnosis of Alzheimer's disease, in conjunction with other methods such as mini-mental state examination (MMSE) score and physician consultation.

The three platelet proteins include at least one isoform of alpha-tropomyosin containing exon 1a and at least two platelet proteins selected from monoamine oxidase-B, coagulation factor XIIIa, wild-type GSTO-1 or mutant GSTO-1.

Preferably, the expression level of monoamine oxidase-B and either wild-type GSTO-1 or mutant GSTO-1 is determined, in addition to an isoform of alpha-tropomyosin containing exon 1a.

Tropomyosin is an actin-binding protein that regulates actin mechanics. Structurally it is a fibrous molecule that consists of an alpha-beta heterodimer containing two alpha-helical structural motifs. Tropomyosin alpha is encoded by the TPM1 gene in humans and has the UniProtKB/SwissProt Primary Accession No. P09493. Tropomyosin beta is encoded by the TPM2 gene in humans and has the UniProtKB/SwissProt Primary Accession No. P07951. In mammals, differential splicing of four highly conserved genes can give rise to more than 40 isoforms of tropomyosin. Furthermore, each isoform can be subject to various degrees of post-translational modification, including phosphorylation and glycosylation.

A number of tropomyosin isoforms have been identified by the present inventors as being useful in the diagnostic method of the invention. Of particular interest in the context of the present invention are isoforms of tropomyosin containing exon 1a (SEQ ID No. 1) and, optionally, isoforms of tropomyosin containing exon 9d (SEQ ID NO. 2).
SEQ ID NO. 1: Leu-Asp-Lys-Glu-Asn-Ala-Leu-Asp-Arg-Ala-Glu-Gln-Ala-Glu-Ala-Asp-Lys-Lys-Ala-Ala
SEQ ID NO. 2: Glu-Lys-Val-Ala-His-Ala-Lys-Glu-Glu-Asn-Leu-Ser-Met-His-Gln-Met-Leu-Asp-Gln-Thr-Leu-Leu-Glu-Leu-Asn-Asn-Met Tropomyosin alpha isoforms useful in the method of the invention are identified herein as S1855, S1827, S1896 and S1941. In one embodiment the at least one isoform of tropomyosin containing exon 1a is S1855. Alternatively, the expression level of at least one isoform of tropomyosin containing exon 1a may be calculated as the sum of the expression of each of the isoforms S1855, S1827, S1896 and S1941. These isoforms are believed to be post-translationally modified variants and are characterized herein using 2-dimensional Difference in Gel Electrophoresis (2D DIGE) and semi-dry Western blots (SD-WB) (see Example 1). The skilled person will be familiar with both of these techniques, which are commonly used in the art.

As used herein, the term 'GSTO-1' refers to the protein identified as EC 2.5.1.18, having the UniProtKB/SwissProt Primary Accession No. P78417 (sequence version 2), or variants and isoforms thereof.

As used herein, the term 'monoamine oxidase' or 'MAO' refers to the protein identified as EC 1.4.3.4, which is an enzyme that catalyses the oxidation of monoamines. In humans there are two forms of MAO, MAO-A which has the UniProtKB/SwissProt Primary Accession No. P21397, and MAO-B which has the UniProtKB/SwissProt Primary Accession No. P27338. Both are present in neurones and astroglia. MAO-A is also present in the liver, gastrointestinal tract and placenta, whereas MAO-B is found in blood platelets.

As used herein, the term "coagulation factor XIIIa" refers to the protein which has the UniProtKB/SwissProt Primary Accession No. P00488 and is encoded in humans by the F13A1 gene. Coagulation factor XIIIa is the catalytically active subunit of coagulation factor XIII and functions in the blood coagulation cascade to stabilise fibrin clots.

The term 'ApoE' is an abbreviation of apolipoprotein E. There are three major isoforms of ApoE, known as ApoE2, E3 and E4, encoded by alleles, ε2, ε3 and ε4 respectively. ApoE3 is the most common isoform. ApoE4 is known to be associated with late-onset Alzheimer's disease, with one or two copies of the ε4 allele representing a greater risk of developing the disease than no copies of the allele. Alzheimer's patients can therefore be categorised as ApoE4 and non-ApoE4 patients.

As used herein, the term 'patient' refers to a mammal, preferably a human, suspected of having Alzheimer's disease or a person thought to have a predisposition to the disease.

In a preferred embodiment, the sample material is derived from a blood sample isolated from the patient. As used herein, the term "blood sample" includes blood components, including platelets, plasma and serum. For example, the sample may be platelet-rich plasma, or isolated blood platelet lysate. The sample material used to for genotyping may be the same as or different from the sample material used to determine protein expression levels. The skilled person will be familiar with standard phlebotomy techniques which are suitable for obtaining a blood sample from a subject.

The term 'Isoform' is defined herein as protein with equivalent function as another protein and a similar or identical sequence but which is encoded by a different gene.

As used herein, the term "gene product" refers to the mRNA or protein product that results from transcription of the gene.

As used herein, the term 'expression level' refers to the amount of the specified protein (or mRNA coding for the protein) in the sampled platelets. Techniques for determining protein expression level will be apparent to the skilled person and include the use of biochip array technology or 2D DIGE.

Preferably, the expression level of specific platelet proteins is quantified in terms of "standardised abundance", which provides a numerical value that takes into account natural variation in the concentration of platelet proteins. The standardised abundance value enables comparison with a known control value.

The term 'peripheral biomarker' is defined as a protein that is present peripherally in blood platelets, wherein alterations in peripheral expression of the protein mirror pathologically significant changes in the CNS, wherein such changes relate to the pathology of Alzheimer's disease.

GSTO-1 genotype distribution is dependent upon the ApoE3 and ApoE4 genotype. Therefore, the decision as to which form of GSTO-1 is included in the method of the invention is made with reference to the number of alleles of ApoE4 in the patient's genome. If the patient has one or two alleles, the expression level of mutant GSTO-1 (aspartic acid (D) at position 140) is determined. If the patient has no ApoE4 alleles then the expression level of wild-type GSTO-1 (alanine (A) at position 140) is determined. Therefore, it will be understood that the number of alleles of ApoE4 in a patient sample determines the identity of the platelet proteins selected for inclusion in the algorithm of the invention.

ApoE4 genotyping can be performed according to Crook et al ("Single-day apolipoprotein E genotyping", J Neurosci Methods [1994] August; 53(2):125-7) and genotyping of wild-type GSTO-1 can be performed according to Veitinger et al ("A combined proteomic and genetic analysis of the highly variable platelet proteome from plasmatic proteins and SNPs", J. Proteomics [2012] August 4).

In a preferred embodiment, the expression level of each of the platelet proteins is determined with a protein assay that determines the protein level accurately.

In a preferred embodiment, the expression level of each of the platelet proteins is determined using a biochip array. A biochip having ligands for the platelet proteins to be detected immobilised on its surface is contacted with a patient platelet cell lysate sample and the surface of the biochip is then washed, such that proteins present in the sample are identified according to detectable interactions formed with immobilised ligands.

In order for ApoE4 genotyping to be conducted at the protein expression level, it is necessary to determine both the ApoE4 protein level and the total ApoE level. Therefore, ApoE4 and/or total ApoE protein expression levels may be determined as part of the method of the invention and included in the algorithms for aiding the diagnosis of Alzheimer's disease.

Total ApoE is also referred to herein as "panApoE", which refers collective all of the different isoforms of ApoE. For example, an antibody that is directed against panApoE will bind to all ApoE isoforms.

Similarly, references herein to "panGSTO-1" encompass both the wild-type and mutant forms of the protein. Therefore, an antibody that is described as being directed against panGSTO-1 will bind to both wild-type and mutant GSTO-1.

In a preferred embodiment, the number of alleles of ApoE4 in a patient's genome is determined at the protein expression level using an ApoE4-specific antibody and, optionally, a panApoE antibody. As shown in Example 3 and Tables 8 and 9 below, at a measured concentration of >19.1 ng/ml, use of an ApoE4 antibody gives 100% sensitivity and specificity for determining the presence of 1 or 2 ApoE4 alleles (Table 8), while use of the ApoE4 to panApoE4 ratio completely discriminates between 0, 1 and 2 allele genomes (Table 9).

A standard method of biomarker statistical analysis is to use univariate methods to compare biomarker levels in various groups and highlight those biomarkers whose concentrations significantly differ between groups.

The individual biomarkers selected for use in the method of the invention are analysed by Receiver Operator Characteristic (ROC) analysis. The ROC curve is a preferred method of assessing the accuracy of a diagnostic test as it addresses both the sensitivity (i.e. the number of true positives) and the specificity (i.e. the number of false positives) of the test. The biomarker(s) which give a high sensitivity and specificity (approximately 80% for both sensitivity and specificity are accepted values in the diagnostic field) form the basis of the logistic regression equation. The value of the measured protein concentration of the biomarker is inputted into the logistic regression equation to give a final value which can be used to aid the diagnosis of Alzheimer's disease.

To construct a ROC curve for multiple biomarkers, a logistic regression equation is derived for the biomarker combination of interest, by inputting measured protein concentration value of each of the biomarkers in a patient's sample into the equation.

Although a logistic regression equation is the preferred statistical method for the current invention, other conventional statistical methods can be used.

By way of example, considering two hypothetical analytes, A and B, the derived logistic regression equation for analyte A and analyte B is:

$$y = 3.2027 \times \log [A] - 0.9506 \times \log [B] + 0.1548$$

wherein [A] is the measured concentration of analyte A and [B] is the measured concentration of analyte B in a patient sample.

If y is above the cut-off value derived in the ROC curve, a diagnosis of Alzheimer's disease in a patient is supported. If y is below the cut-off value, the diagnosis of Alzheimer's disease is not supported.

The terms "control value" and "cut-off" are used interchangeably herein, and refer to a reference value against which the value obtained for the patient sample according to the method of the invention is compared in order to aid the diagnosis of Alzheimer's disease.

In order to obtain the control value, the expression level of the platelet proteins listed in step (i) of the method of the invention is determined from samples of a population of healthy individuals. The statistical tools of ROC curve analysis and linear regression are then applied to the results in order to obtain a single cut-off value.

It will be appreciated that the cut-off value will vary according to the size of the control population. Biological variation within the control population is reduced by increasing the size of the population. Therefore it is preferable if the control value is derived from a control population comprising at least 30 healthy individuals, preferably at least 50 healthy individuals and more preferably at least 100 healthy individuals.

A further embodiment of the method of the invention provides four different models for the diagnosis of Alzheimer's disease; these are summarized in Table 1. In this context, "Exon 1a" refers to the sum of the expression (standardised abundance) of each of the tropomyosin-alpha isoforms S1855, S1827, S1896 and S1941.

Each of the models uses two different algorithms that take account of the over-representation of wtGSTO-1 in non-ApoE4 Alzheimer's disease patients. The use of the respective algorithm depends on the presence or absence of ApoE4 in the patient, thereby accounting for the over-representation of wt GSTO-1 in non-ApoE4 patients. The result is obtained by applying a weight factor to the standardised abundance of each biomarker. Weighting factors can be applied to the expression values of each of the biomarkers, and these may differ for different biomarkers and depending upon whether the assay is being conducted using a biochip or 2D DIGE.

In its simplest form, using a weighting factor of 1 for all biomarkers, the result for a test subject would be by applying the following calculation:

1×standardised abundance (Mao-B)+1×standardised abundance (total tropomyosin)+1×standardised abundance (coagulation factor XIIIa)+1×standardised abundance (wtGSTO-1)+1×standardised abundance (ApoE4).

The result is then compared to the control value. A result higher than the control is indicative of Alzheimer's disease in the patient.

Model 1

Model 1 uses two different algorithms that take account of the over-representation of wtGSTO-1 in non-ApoE4 Alzheimer's disease patients. The use of the respective algorithm depends on the presence or absence of ApoE4 in the patient, thereby accounting for the over-representation of wt GSTO-1 in non-ApoE4 patients. If the ApoE4 allele is absent from the patient sample, Algorithm A is used. Otherwise, Algorithm B is used.

Model 2

Model 2 also uses two different algorithms. If the ApoE4 allele is absent from the patient's genome then Algorithm C is applied. If the patient carries 1 or 2 ApoE4 alleles then Algorithm B is applied.

Model 3

Model 3 also uses two different algorithms. If the ApoE4 allele is absent from the patient's genome then Algorithm D is applied. If the patient carries 1 or 2 ApoE4 alleles then Algorithm E is applied.

Model 4

Model 4 also uses two different algorithms. If the ApoE4 allele is absent from the patient's genome then Algorithm F is applied. If the patient carries 1 or 2 ApoE4 alleles then Algorithm G is applied.

The resulting value calculated using the algorithms of Models 1, 2, 3 or 4 is compared to a pre-determined control value in order to aid the diagnosis of disease.

Each of the algorithms described in the above Models 1-4 can also comprise a weighting factor based on the number of alleles of ApoE4 present in the patient's genome. If the patient carries one or two alleles of ApoE4, a value of +1 or +2 respectively is added to the total standardised abundance value for all of the platelet proteins that are included in a given algorithm. The resulting value is then compared to the control in order for a diagnosis to be made. Alternatively, if the patient has no alleles of ApoE4 then no additional weighting factor is added to the total standardised abundance value.

The advantage of the biomarker combinations used in the algorithms of the invention is that they provide more accurate diagnostic results than other biomarker combinations known in the art.

According to the present invention, the diagnosis of Alzheimer's disease can be aided by comparing the total expression level of each of the biomarkers in the isolated platelet sample to a control value. Diagnosis of disease may be achieved in combination with other factors such as clinical observations and patient history, and by reference to previous assay results from the patient.

However, since platelets are differently concentrated in the blood, the concentration of platelet proteins also varies. The coefficient of variation for platelet concentration in platelet-rich plasma and gel-filtrated platelets is 38% and 32% respectively, and the correlation of the of the platelet count to the platelet concentration is poor (K=0.58 for an analytical normalisation of platelet biomarkers by the platelet count). This makes the concentration of platelet proteins in a blood sample an unreliable indicator for determination of pathological changes in the brain and additional steps to normalise platelet protein concentrations are required.

Therefore, the present invention utilises internal extraction standards to enable the accurate quantification of expression of platelet proteins in terms of "standardised abundance".

In a preferred embodiment, internal extraction standard is derived from the human platelet proteome and is present in a patient sample, or control sample, of platelet lysate.

As used herein, the term low biological variation' refers to cell extract proteins with a CV value of less than 0.18.

As used herein, the term 'normalise natural biological variation' refers to the use of a reference value corresponding to the concentration of a protein which varies negligibly between samples, against which the concentration of proteins with higher natural variation between samples can be accurately determined.

Candidate proteins for internal extraction standards were identified by analysing the biological variation of 908 different proteins within the platelet proteome of 110 individu-

TABLE 1

| | | | Algorithm contains: | | | | | |
| --- | --- | --- | --- | --- | --- | --- | --- | --- |
| | | | Standardised abundance of (2D-DIGE) | | | | | |
| Model | Algorithm | Applied to patients | Mao-B | Tropomyosin S1855 | Tropomyosin Exon 1a | Coagulation Factor S921 XIIIa | wt GSTO-1 (Ala 140) | Mutant GSTO-1 (D140) |
| 1 | A | ApoE4-negative | X | X | X | — | X | — |
| | B | ApoE4-positive | X | X | X | — | — | — |
| 2 | C | ApoE4-negative | X | X | X | — | X* | — |
| | B | ApoE4-positive | X | X | X | — | — | — |
| 3 | D | ApoE4-negative | X | X | — | — | X | — |
| | E | ApoE4-positive | X | X | — | — | — | X |
| 4 | F | ApoE4-negative | X | — | X | — | X | — |
| | G | ApoE4-positive | X | — | X | — | — | X |

X The respective assay is included in the algorithm
— The respective assay is not included in the algorithm
*Weighting factor of 0.5 applied als, using bioinformatic analysis, mass spectrometry and 2D PAGE. Table 2 lists candidates with a low biological variation identified on gels with the pH range of 4-7. Table 3 lists candidates with a low biological variation identified on gels with the pH range of 6-9.

TABLE 2

| Protein Name | SwissProt Accession No. | CV-all |
|---|---|---|
| 14-3-3 gamma | P61981 | 0.084 |
| Peroxiredoxin-6 | P30041 | 0.086 |
| Growth factor receptor-bound protein 2 | P62993 | 0.088 |
| F-actin capping protein beta subunit (Cap Z beta) | P47756 | 0.088 |
| Serine/threonine-protein phosphatase PP1-alpha catalytic subunit | P62136 | 0.089 |
| Myosin light protein 6 | P60660 | 0.092 |
| Microtubule-associated protein RP/EB family member 2 | Q15555 | 0.092 |
| Rab GDP dissociation inhibitor beta (Rab GDI beta) | P50395 | 0.093 |
| Programmed cell death 6-interacting protein (PDCD6-interacting protein) | Q8WUM4 | 0.095 |
| Alpha-soluble NSF attachment protein (SNAP-alpha) | P54920 | 0.095 |
| Guanine nucleotide-binding protein G(I)/G(S)/G(T) subunit beta 1 | P62873 | 0.095 |
| 14-3-3 protein theta | P27348 | 0.099 |
| 14-3-3 protein zeta/delta | P63104 | 0.099 |
| GRP75 Mortalin | P38646 | 0.104 |
| Protein disulfide-isomerase A6 | Q15084 | 0.112 |
| Integrin α-IIb | P08514 | 0.143 |
| Nucl. Assembly prot 1 | P55209 | 0.177 |

TABLE 3

| Protein Name | SwissProt Accession No. | CV-all |
|---|---|---|
| Mitogen-activated protein kinase 1 (ERK2) | P28482 | 0.103 |
| Profilin-1 | P07737 | 0.074 |
| Cyclophilin A | P62937 | 0.082 |
| Cyclophilin A | P62937 | 0.092 |
| Triosephospahate-Isomerase | P60174 | 0.103 |
| Voltage-dependent anion-selective channel protein 3 | Q9Y277 | 0.112 |
| Fructose-bisphosphate aldolase A | P04075 | 0.115 |
| Calponin-2 (Calponin H2; smooth muscle) (Neutral calponin) | Q99439 | 0.115 |
| Tyrosyl-tRNA synthetase; cytoplasmic | P54577 | 0.120 |
| Dual specificity protein phosphatase 3 | P51452 | 0.121 |
| Actin-related protein 2/3 complex subunit 2 | O15144 | 0.125 |
| Isocitrate Dehydrogenase | P48735 | 0.128 |
| Protein-L-isoaspartate (D-aspartate) O-methyltransferase | P22061 | 0.128 |
| Glyceraldehyde-3-phosphate dehydrogenase | P04406 | 0.129 |
| Proteasome subunit alpha type 2 | P25787 | 0.129 |
| Proteasome subunit alpha type 4 | P25789 | 0.137 |
| Proteasome subunit alpha type 7 | O14818 | 0.147 |
| Glyceraldehyde-3-phosphate dehydrogenase | P04406 | 0.155 |

Suitable proteins may be identified according to their SwissProt Primary Accession Numbers. The SwissProt accession number identifies the mRNA product that codes for each protein.

The UniProtKB/SwissProt protein knowledgebase is an annotated protein sequence database established by the merger of the SwissProt and UniProt knowledgebase protein databases. It is maintained collaboratively by the Swiss Institute for Boinformatics (SIB), the European Bioinformatics Institute (EBI) and the National Biomedical research Foundation. The UniProtKB/SwissProt release referred to herein is v55.2, of 8 Apr. 2008, and can be accessed at http://expasy.org/sprot.

All proteins deriving from this mRNA are within the scope of the invention, i.e. all variants and post-translational modifications.

In a preferred embodiment of the invention, the internal extraction standard protein is 14-3-3 protein gamma or ERK2.

A second aspect of the present invention provides a biochip which comprises a solid support comprising discrete test regions in which ligands for at least three platelet proteins selected from monoamine oxidase-B, coagulation factor XIIIa, tropomyosin isoforms S1855, S1827, S1896 and/or S1941, wild-type GSTO-1 protein and/or mutant GSTO-1 protein are immobilised. The biochip may be used in the method of the invention described above.

Preferably, the biochip comprises one or more ligands of at least one isoform of alpha-tropomyosin containing exon 1a, and one or more ligands of at least two platelet proteins selected from monoamine oxidase-B, coagulation factor XIIIa, alpha-tropomyosin containing exon 1a, wild-type GSTO-1 protein and/or mutant GSTO-1 protein immobilised thereon. The biochip may also comprise immobilised ligands for ApoE and/or ApoE4.

In a preferred embodiment, the biochip comprises one or more ligands for at least one isoform of alpha-tropomyosin containing exon 1a, Mao-B, wild-type and/or mutant GSTO-1 (which may include ligands against pan GSTO-1), ApoE4 and/or panApoE and one or more internal extraction standard proteins selected from Tables 2 and/or 3, preferably ERK2 and/or 14-3-3 protein gamma.

An example of a biochip according to the invention is shown schematically in

FIG. 1. (A) shows antibodies directed against the proteins of interest spotted on individual discrete test regions, incubated with samples or calibrators and the target analyte concentrations quantified by measuring the relative light units of bound HRP-labeled secondary antibodies. (B) illustrates determination of the GSTO1-(black squares) and APOE-(circles) genotypes with the protein biochip. Together with the image in (A), all four possible combinations (APOE ε4−/GSTO1*A140, APOE ε4+/GSTO1*A140, APOE ε4−/GSTO1*D140, APOE ε4+/GSTO1*D140) are shown. The number of GSTO1*A140- and ApoE4-alleles was defined according to the individual protein concentrations. (C) shows the resulting AUC of the ROC of 0.969 (n=102).

The selection of ligands immobilised on the biochip may be determined according to the ApoE4 genotype of a given patient, as described in respect of the first aspect of the invention.

Use of the biochip of the invention enables multi-analyte screening of the patient sample in a rapid, accurate and easy to use format. The multi-analyte approach has benefits beyond time and cost savings, which are vital in the drive towards increasing efficiencies and improved clinical performance. Traditional diagnosis takes the form of single analyte assays, even though several are usually required, thus increasing sample volumes, possibly requiring multiple patient attendance and increasing the time before diagnosis. The multi-analyte assay reduces patient discomfort, as all the assays are conducted using a single patient sample, negating the need for multiple patient sampling.

As used herein, the term ligand' refers to a molecule that binds to a target. The ligands of the biochip of the invention may be antibodies, antigens or nucleic acids. Preferably, the one or more ligands are antibodies, preferably monoclonal antibodies. The term "monoclonal antibodies" refers to a homogenous population of antibodies (including antibody fragments), which recognise a single epitope on a target.

If only genotyping data for (wt) GSTO-1 and (mt) GSTO-1 are included in the models then the assays for wild-type (wt) GSTO-1 and mutant (mt) GSTO-1 are interchangeable. If genotyping via the protein expression level is possible the protein assays for (wt) GSTO-1 and (mt) GSTO-1 are also interchangeable. However, the use of genotyping data only will result in decreased accuracy of diagnosis, since the models perform better when the respective protein concentrations are used.

The expression of the specific platelet proteins in a patient sample according to the invention is quantified in terms of standardised abundance, preferably using a biochip array system. The biochip of the invention is contacted with a patient platelet cell lysate sample and then washing the surface, such that proteins present in the sample are identified according to the interactions formed with ligands immobilised on the biochip surface. Ligand-protein interactions produce chemiluminescent signals that can be rapidly detected and analysed using an imaging system, such as a charge-coupled device (CCD) super cooled camera, to simultaneously quantify the individual analytes. Sample addition to the biochip and the subsequent wash, incubation and signal reagent steps can be either entirely automated or by manual application. The results of the platelet protein expression measurement undergo two consecutive normalisation procedures. The first involves a procedure for the correction of technical variation of the signals that are obtained with the biochip array system, such as background correction, reference spot and correction spot validation.

Comparisons of signals of the unknown sample with calibration curves give the protein concentrations of the unknown sample. The platelet concentration in whole blood and in the isolated samples varies between individuals and hence affects the AD biomarker protein concentration in the samples. Therefore, a second standardisation procedure, the calculation of the standardised abundance of the Alzheimer's disease biomarkers, is necessary. One or more internal extraction standard proteins (selected from Tables 3 and 4) are measured in parallel with the Alzheimer's disease biomarkers. The standardised abundance value corresponds to the ratio between the expression levels of the Alzheimer's disease biomarker and the internal extraction standard, or the sum of multiple internal extraction standards.

Alternatively, expression levels can be determined using a 2D DIGE analysis and calculating the standardised abundance of the respective spots on the gel using software such as the DeCyder software 6.5 (GE Healthcare).

In the 2D DIGE system, there are also two consecutive procedures used to obtain the standardised abundance of a protein. The first procedure (the normalization) involves the calculation of a normalisation factor by calculating a data histogram from spot ratios between the primary and the secondary gel images. A normal distribution curve is fitted to the histogram and the resulting centre of the model curve is the normalisation factor. The spot volumes in the primary spot map are then normalised using the normalisation factor $$C': V1i' = V1i \times 10C(ii)$$

wherein: V1 i' is the normalised volume of spot i in the primary gel image; and V1i is the volume of spot i in the primary gel image The second procedure involves the use of an internal standard that usually is a pool of all samples tested in the study and is present on each 2-dimensional DIGE gel. The standardized volume ratio for each standard image from the different gels is set to the value 1.0. The expression ratio for each sample spot is then related to its corresponding standard spot in the same gel, thus making it possible to compare ratios between matched protein spots in the different gels.

The resulting standardised abundance value is the ratio between the normalised protein spot volume and the normalised internal standard spot volume described in terms of fold change.

The above-mentioned calculations can be modified by the use of Logo of the standardised values in order to aid scaling in graphical representations and statistical analyses.

The following non-limiting examples illustrate aspects of the invention.

Example 1

Method

49 Alzheimer's disease patients (mean age=81±8.2 years) and 52 age- and sex-matched control individuals (mean age=80±8.5 years) were analysed by 2-dimensional differential gel electrophoresis (2D DIGE). Furthermore, the ApoE4 genotype and the polymorphism rs4925 of GSTO-1 at amino acid position 140 (alanine versus aspartate) of these individuals were determined.

Algorithms of the most significant LOAD-biomarkers were generated using simple sum scores and were assessed by Receiver operating characteristic (ROC) curves and Area under the curve (AUC).

Study Cohorts

This study was designed as a two stage pilot for the identification of AD biomarkers in the platelet proteome by 2D DIGE. For this reason a statistical evaluation was made from both pH ranges from the discovery set. From these training cohorts the biomarkers were selected and concomitant statistically evaluated in a second verification stage. Only those protein spots were chosen in training phase that were present in more than 80% of the 2D DIGE gels, showed expression changes larger than 20% and significances were defined for an unadjusted Wilcoxon test with a P value <0.05. As shown in Table 4, ApoE genotypes and allele frequencies showed major differences between cases and controls; the E4 allele frequency being 63% in the AD group and 9.8% in controls (P<0.001).

TABLE 4

| | Discovery Set | | Verification Set | |
| --- | --- | --- | --- | --- |
| | AD (n = 22) | Control (n = 25) | AD (n = 27) | Control (n = 27) |
| Mean age (SD) | 81 (±8.2) | 80 (±8.5) | 83 (±6.8) | 81 (±7.4) |
| MMSE | 5.5 (±4.2) | 28.5 (±0.8) | 14 (±6.7) | 29 (±0.9) |
| % female | 82 | 82 | 81 | 81 |
| % ApoE ε4/* | 68 | 8 | 59 | 11 |
| % ApoE ε4/4 | 27 | 0 | 7 | 0 |

Single AD Biomarkers

Table 5a shows results for confirmed AD cases (n=9), which are a subgroup of the included AD patients and were statistically matched with the appropriate controls from the respective 2D DIGE gels. The tropomyosin isoforms to be detected contain exon 1a and optionally exon 9d; tropomyosin isoforms P09493-3 comprise exons 1a and 9d, while tropomyosin isoform P09493-1 incorporates exon 1a but not exon 9d.

TABLE 5a

| Spot IP | Acession No. | protein identity | Discovery ratio (AD/Controls) | Discovery unadjusted p-value | Verification ratio (AD/Controls) | Verification unadjusted p-value | All ratio (AD/Controls) | All unadjusted p-value | All adjusted p-value | Confirmed AD ratio (AD/Controls) | Confirmed AD unadjusted p-value |
|---|---|---|---|---|---|---|---|---|---|---|---|
| S1929 | P02649 | Apolipoprotein ε4 | 3.31 | 0.000 | 1.48 | 0.138 | 2.21 | 0.000 | 0.118 | 1.96 | 0.020 |
| B645 | P27338 | Monoamine oxidase B | 1.28 | 0.000 | 1.60 | 0.000 | 1.44 | 0.000 | 0.001 | 1.38 | 0.001 |
| S1942 | P02649 | Apolipoprotein ε3 | 0.57 | 0.000 | 0.56 | 0.014 | 0.56 | 0.000 | 0.023 | 0.46 | 0.001 |
| S1855 | P09493 | α-Tropomyosin | 1.45 | 0.001 | 1.26 | 0.006 | 1.34 | 0.000 | 0.054 | 1.54 | 0.001 |
| S921 | P00488 | Coagulation factor XIIIa | 1.27 | 0.004 | 1.19 | 0.239 | 1.23 | 0.005 | 0.118 | 1.30 | 0.030 |
| B330 | Q01813 | 6-phophofructokinase type C | 0.80 | 0.017 | 0.98 | 0.588 | 0.92 | 0.182 | 0.962 | 0.93 | 0.512 |
| S458 | P18206-2 | Vinculin | 1.21 | 0.031 | 1.02 | 0.749 | 1.12 | 0.256 | 0.850 | 1.20 | 0.100 |
| | | Further Isoforms of α-Tropomyosin/XIIIa which were indistinguishable by mass spectrometry from S1855/S921 and their summarised SA: | | | | | | | | | |
| S1827 | P09493 | α-Tropomyosin | 1.22 | 0.092 | 1.11 | 0.073 | 1.16 | 0.014 | 0.440 | 1.36 | 0.005 |
| S1896 | P09493 | α-Tropomyosin | 1.13 | 0.218 | 1.07 | 0.132 | 1.10 | 0.041 | 0.388 | 1.17 | 0.282 |
| S1941 | P09493 | α-Tropomyosin | 1.13 | 0.141 | 1.01 | 0.979 | 1.06 | 0.309 | 0.680 | 1.27 | 0.051 |
| SUM | P09493 | α-Tropomyosin | 1.19 | 0.035 | 1.16 | 0.046 | 1.18 | 0.002 | 0.365 | 1.29 | 0.034 |
| S912 | P00488 | Coagulationfactor XIIIa | 0.81 | 0.371 | 1.14 | 0.020 | 0.98 | 0.512 | 1.000 | 0.60 | 0.090 |
| S916 | P00488 | Coagulationfactor XIIIa | 1.22 | 0.014 | 1.10 | 0.276 | 1.15 | 0.156 | 0.782 | 1.23 | 0.068 |
| SUM | P00488 | Coagulationfactor XIIIa | 1.11 | 0.321 | 1.13 | 0.570 | 1.12 | 0.014 | 0.485 | 1.10 | 0.422 |

Table 5b shows further AD-related changes in the 2D DIGE platelet proteome of the pH 4-7 (S) and 6-9 (B) range of only ApoE E4 negative AD patients. The proteins are listed regarding their unadjusted P values (Wilcoxon). The filter includes only significant changed proteins which are matched in more than 80% of the analysed gels, unadjusted P value smaller than 0.001 and ratios of their SA values from the AD (n=15) to matched controls (n=15) smaller than 0.8 or larger 1.2

TABLE 5b

| Spot ID | Acession No. | protein identity | match % | ratio AD/Control | unadjusted P value | adjusted P value |
|---|---|---|---|---|---|---|
| S2000 | P78417 | Glutathione S-transferase Omega 1 rs4925 = GSTO1*D140 | 100 | 0.45 | 0.000 | 0.625 |
| S1998 | P78417 | Glutathione S-transferase Omega 1 wild type = GSTO1*A140 | 100 | 1.53 | 0.000 | 0.814 |

Figure 2:
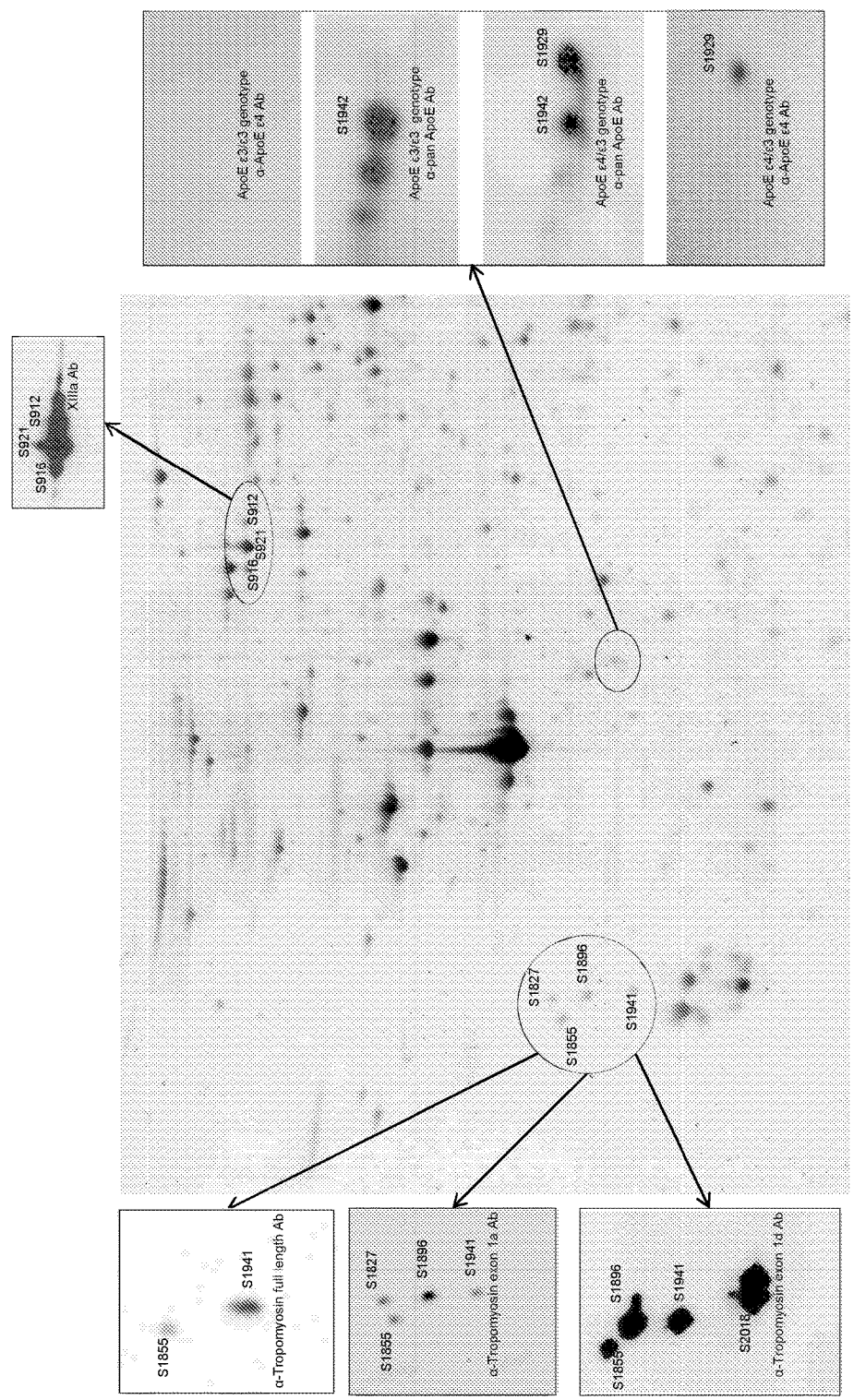
FIG. 2 shows the validation of AD biomarker identifications by 2D Western Blot.

Validation of AD biomarker identifications by 2D Western Blot is shown in FIG. 2. This typical 2D-gel image of blotted the platelet proteome in the pH range 4-7 on nitrocellulose membrane was visualised by the total protein stain RuBPS. Protein spots are labelled with the protein accession numbers and spot ID from the master of the respective DeCyder BVA evaluation. The cut outs are details of the 2D Western Blots labeled with the antibodies. The 2D images of the specific tropomyosin antibody signals were overlaid to the respective total protein stain RuBPS of the blotted protein spots to validate the MS identifications. The ApoE spots were not visible by the total protein stain RuBPS.

Combination Biomarker AD Algorithm

Table 6 shows the standardised abundance (SA) of significant platelet protein spots obtained from 2D DIGE analysis using the DeCyder software and combined with APO ε4 allele count with a simple summation of all these values. The classification of Models 5-8 (which correspond to Models 1-4 respectively in Table 1) into (a) and (b) means that in algorithms (a) wt GSTO1 A140 SA spot values were only included when the individual was not carrying APO ε4, whereas in algorithm (b) mutant GSTO1 D140 was included when the individual was APO ε4 carrier. In the context of this table, the values for tropomyosin Exon 1a consist of the SA sum of the tropomyosin isoforms S1855, S1827, S1896 and S1941.

The best results are indicated by the highest AUC values for both discovery and verification groups. Therefore, as can be seen from this data, the biomarker combinations of Models 7 (a and b) and 8 (a and b) were found to be the best, with the highest AUC values for discovery AUC and verification AUC.

TABLE 6

| | Model contains | | | | | | | | | | |
|---|---|---|---|---|---|---|---|---|---|---|---|
| | Standardised Abundances of (2D-DIGE) | | | | | | | | | | |
| Model | Mao-B B645 | Tropomyosin S1855 | Tropomyosin Exon 1a | Coagul factor S921 XIIIa | wt GSTO1 A140 | rs4925 GSTO1 D140 | Genotyping: Alleles of Apo ε4 | AUC | CI lower | CI upper | Discovery AUC | Verification AUC |
| 0 | + | − | − | − | − | − | − | 0.881 | 0.788 | 0.934 | 0.841 | 0.883 |
| 1 | + | − | − | − | − | − | + | 0.911 | 0.854 | 0.968 | 0.894 | 0.929 |
| 2 | + | + | − | − | − | − | + | 0.917 | 0.862 | 0.971 | 0.888 | 0.933 |
| 3 | + | + | − | + | − | − | + | 0.897 | 0.834 | 0.960 | 0.894 | 0.905 |
| 4 | + | + | − | − | + | − | + | 0.896 | 0.837 | 0.954 | 0.900 | 0.894 |

TABLE 6-continued

| | Model contains | | | | | | | | | | | |
|---|---|---|---|---|---|---|---|---|---|---|---|---|
| | Standardised Abundances of (2D-DIGE) | | | | | | | | | | | |
| Model | Mao-B B645 | Tropomyosin S1855 | Tropomyosin Exon 1a | Coagul factor S921 XIIIa | wt GSTO1 A140 | rs4925 GSTO1 D140 | Genotyping: Alleles of Apo ε4 | AUC | CI lower | CI upper | Discovery AUC | Verification AUC |
| 5a | + | + | + | − | + | − | − | 0.868 | 0.800 | 0.936 | 0.882 | 0.867 |
| 5b | + | + | + | − | − | − | + | | | | | |
| 6a | + | + | + | − | + | − | − | 0.927 | 0.879 | 0.974 | 0.931 | 0.927 |
| 6b | + | + | + | − | − | − | + | | | | | |
| 7a | + | + | − | − | + | − | − | 0.964 | 0.934 | 0.994 | 0.938 | 0.982 |
| 7b | + | + | − | − | − | + | + | | | | | |
| 8a | + | − | + | − | + | − | − | 0.946 | 0.905 | 0.987 | 0.907 | 0.981 |
| 8b | + | − | + | − | − | + | + | | | | | |

Results

Several algorithms that contain combinations of the LOAD biomarkers of alpha-tropomyosin isoforms containing exon-1a, together with a combination of biomarkers for ApoE4, monoamine oxidase B, glutathione S-transferase omega wild type (wtGSTO-1) and/or mutant (mutGSTO-1) showed AUC above 0.9. Best AUC were obtained when the finding that wtGSTO-1 is prominent in non-ApoE4 LOAD patients was taken into consideration, e.g.

Model 1: AUC=0.911
(95% confidence interval 0.85-0.97)
Model 7: AUC=0.964
(95% confidence interval 0.93-1.00)

Figure 3A:
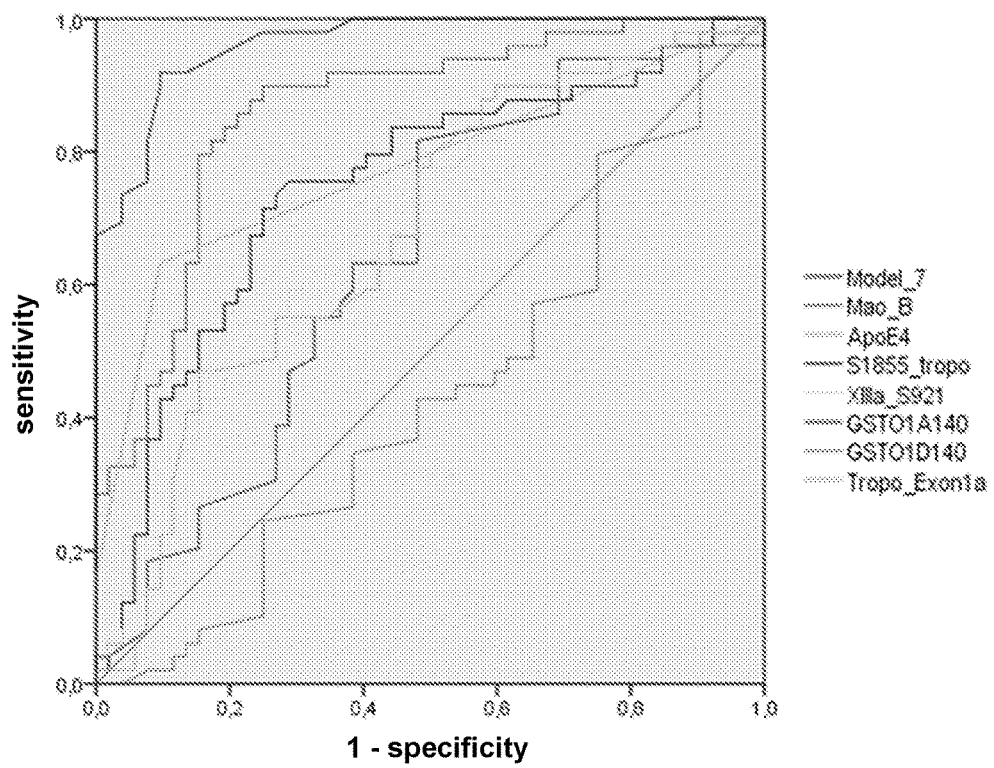
FIG. 3 (A) shows ROC curves of single AD biomarker and (B) is a scatter diagram for a combination of four AD biomarkers.
Figure 3B:
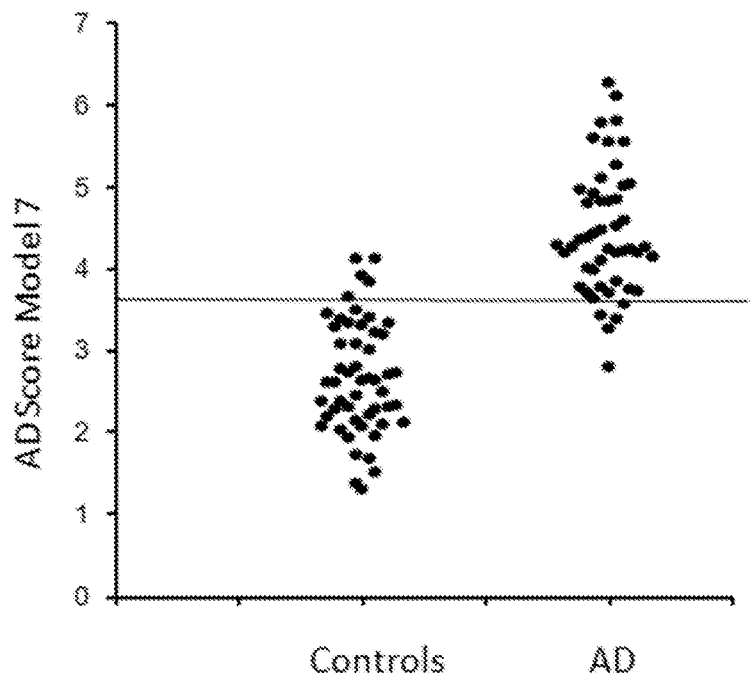

FIG. 3 (A) shows ROC curves of single AD biomarker and FIG. 3 (B) is a scatter diagram for the combination model 7 using four AD biomarkers (Mao-B, Tropomyosin, GSTO-1 and Apo ε4) results in an AUC value of 0.964 with 90% sensitivity and 90% specificity (cutoff, 3.7).

Figure 4:
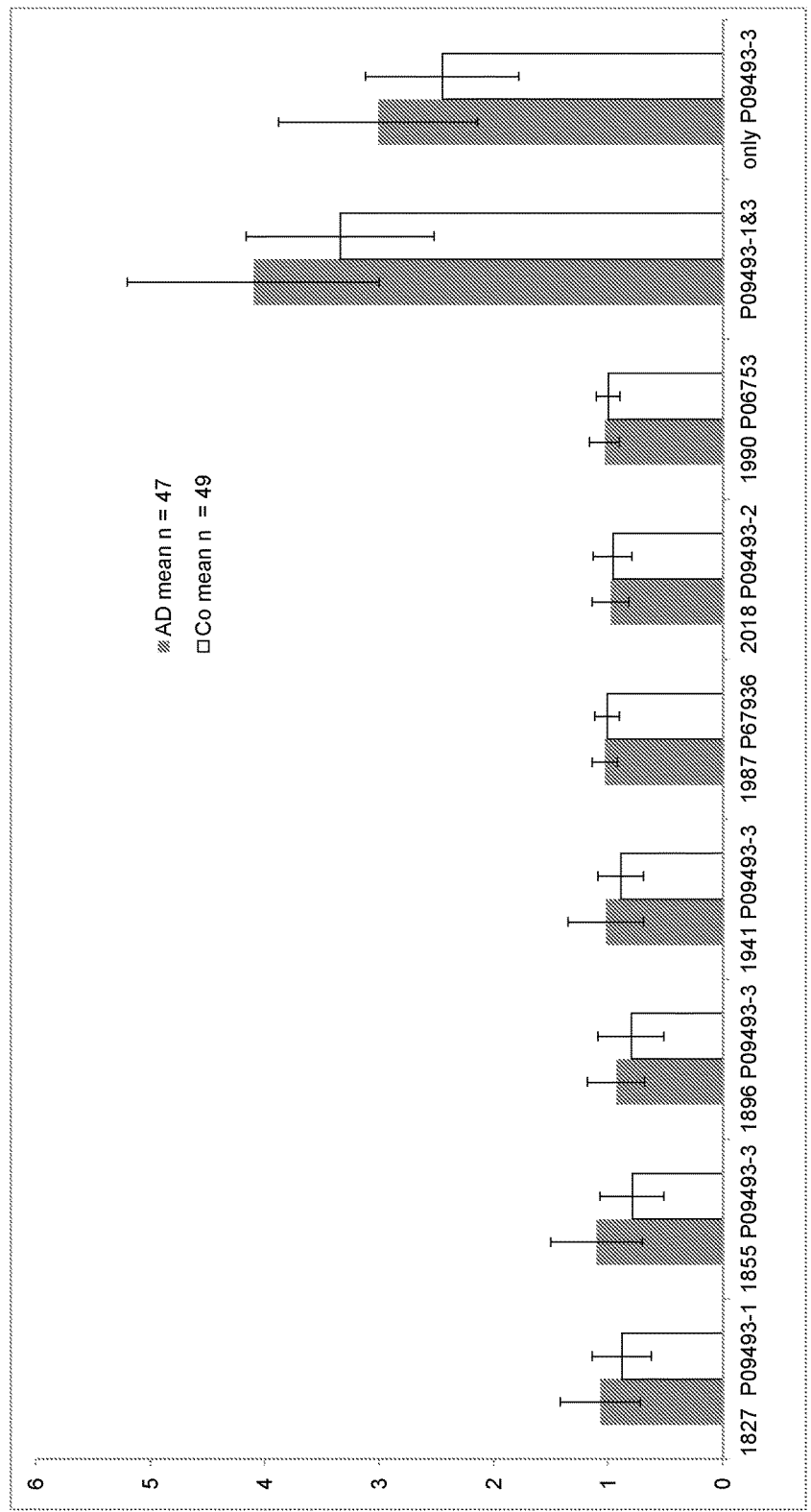
FIG. 4 is a graph showing that tropomyosin isoforms containing 1A and 9D exons are up-regulated in AD.

FIG. 4 is based in the data in Table 7. This data shows that tropomyosin isoforms containing 1A and 9D exons are up-regulated in AD.

Consequently, two monoclonal anti-GSTO-1 antibodies were developed, one directed against the A140 wild type (wt) and one against panGSTO-1 (to detect wt and mutant GSTO-1) [27]. Similarly, to distinguish the ApoE isoform E4 from E2 and E3, which differ in two amino acids at positions 112 and 158, a monoclonal antibody highly specific for the E4 isoform was generated. Antibodies to exons 1a and 9d are also described in the literature, for example Gunning et al 2005, Trends in Cell Biology, Vol. 15: 333-341.

Figure 6:
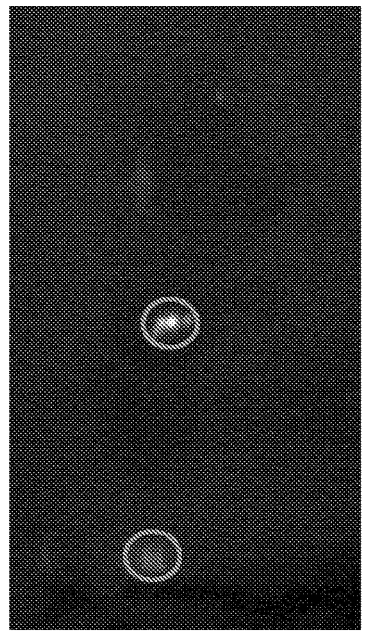
Figure 6:
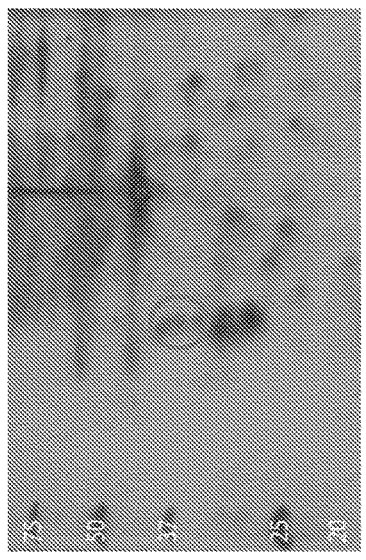
Figure 6:
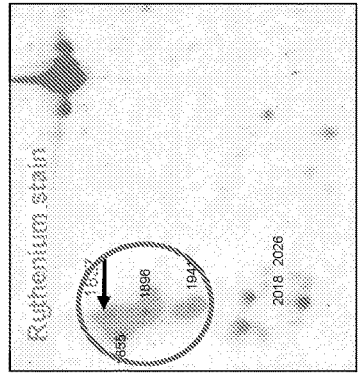

In order to generate the data shown in FIG. 6, 15 μg TCA-precipitated/urea-resolubilised T228 GFPs were separated on a pH 4-7 strip (7 cm) in the first dimension with subsequent MW-separation under denaturing conditions and WB-detection on a PVDF-membrane. The silver-stain confirms a satisfying separation of platelet protein and presence of the sought Tropomyosin chain. The actin-spot which can be observed results from previous staining with specific anti-pactin antibody.

Figure 7:
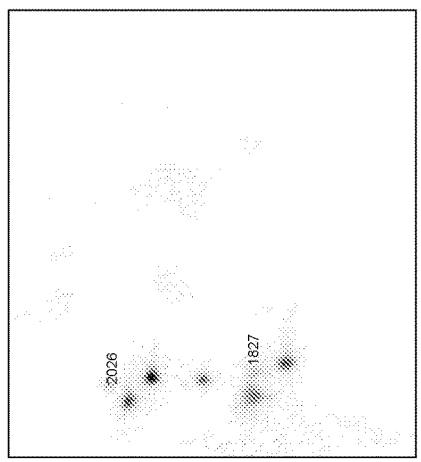
FIG. 7 shows 2D-Western Blot evaluation of tropomyosin exon 9d.
Figure 7:
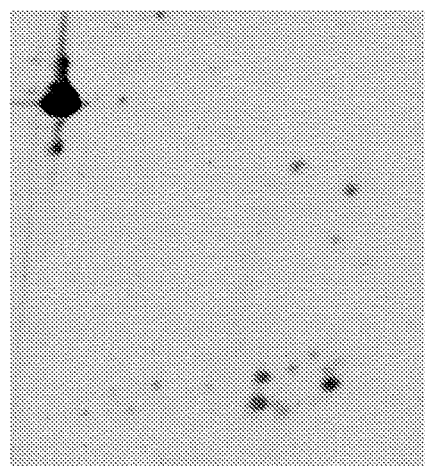
Figure 7:
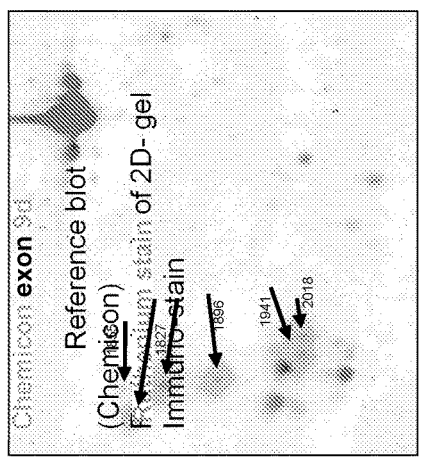

In order to generate the data shown in FIG. 7, 45 μg TCA-precipitated/urea-resolubilised GFP were separated on

TABLE 7

| | Tropomyosin Isoforms | | | | | | | | |
|---|---|---|---|---|---|---|---|---|---|
| | 1827 P09493-1 | 1855 P09493-3 | 1896 P09493-3 | 1941 P09493-3 | 1987 P67936 | 2018 P09493-2 | 1990 P06753 | P09493-1&3 | only P09493-3 |
| AD mean | 1.07 | 1.1 | 0.93 | 1.02 | 1.03 | 0.98 | 1.03 | 4.1 | 3.01 |
| Co mean | 0.88 | 0.79 | 0.8 | 0.89 | 1.01 | 0.96 | 1 | 3.34 | 2.45 |
| AD SD | 0.35 | 0.40 | 0.25 | 0.33 | 0.11 | 0.16 | 0.13 | 1.10 | 0.87 |
| Co SD | 0.26 | 0.28 | 0.29 | 0.20 | 0.11 | 0.17 | 0.10 | 0.82 | 0.67 |
| % change AD | 121 | 139 | 118 | 115 | 102 | 103 | 102 | 123 | 123 |
| tTest 2-side | 0.03104 | 0.00008 | 0.00952 | 0.04883 | 0.68447 | 0.68293 | 0.36702 | 0.00043 | 0.00037 |

Figure 5:
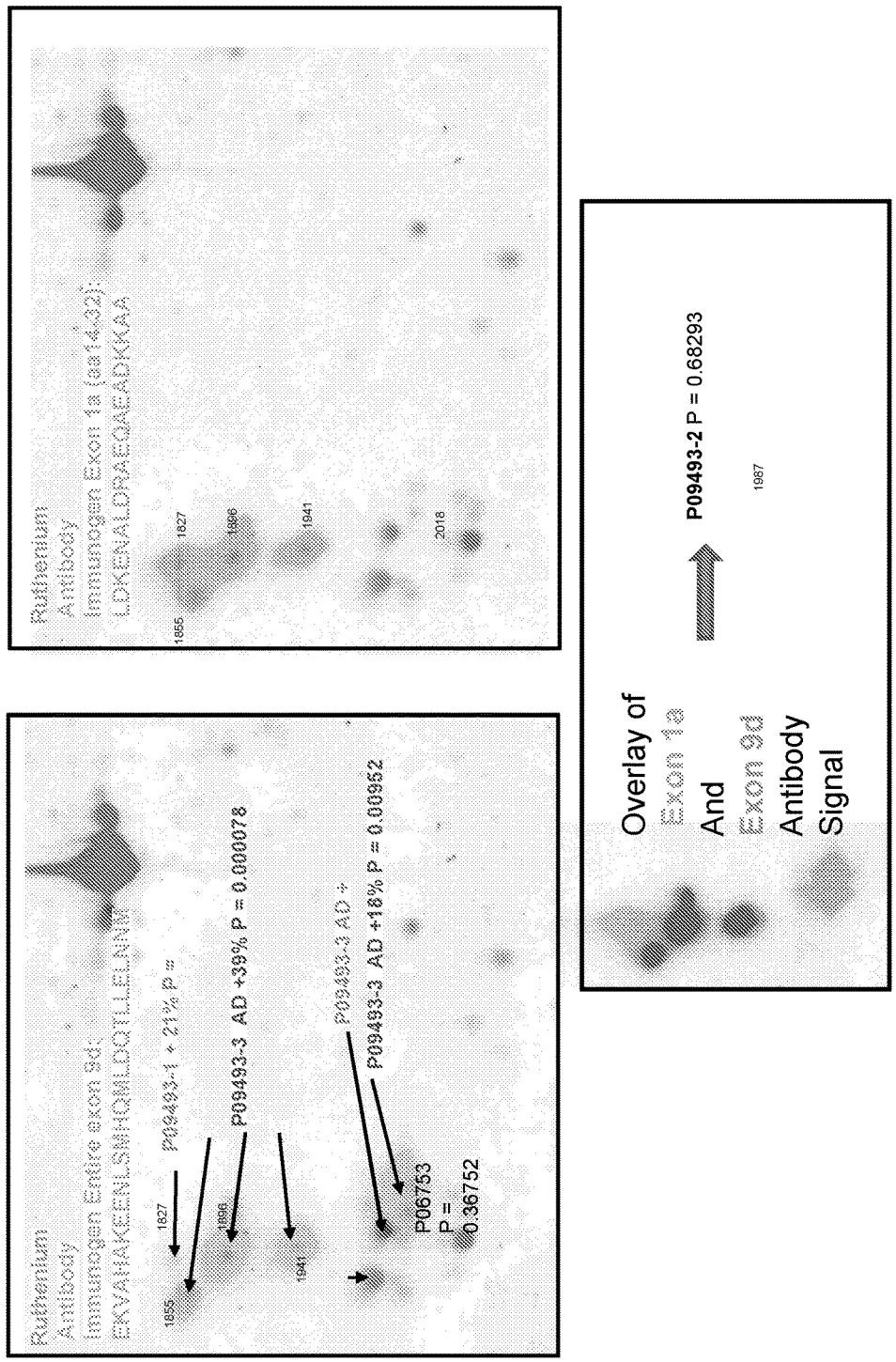
FIG. 5 shows the identification of AD-specific tropomyosin isoforms using commercial reference antibodies.

AD-specific tropomyosin isoforms are further characterised in FIG. 5. This figure shows the identification of tropomyosin isoform P09493-3 using commercial reference antibodies.

FIGS. 6 and 7 show 2D-WB evaluation of tropomyosin exon 1a and exon 9d, respectively. The inventors generated suitable antibodies for detection of the exon 1a and 9d sequences of Tm1. Peptides corresponding to SEQ ID NOs 1 and 2 were conjugated to bovine serum albumin (BSA), via the addition of N-terminal cysteine residues, and used for immunization. As the GSTO-1*D140 and ApoE4 protein isoforms are caused by single nucleotide polymorphisms (SNPs), further highly specific antibodies were required.

a pH 4-7 strip (24 cm) in the first dimension with subsequent MW-separation under denaturing conditions and WB-detection on a PVDF-membrane.

Example 2

The inventors investigated the translation of the proteomic 2D-DIGE results to the new protein biochip technique by conducting statistical analysis of 51 AD and 51 control samples with either 2D-DIGE or the novel protein biochip of the invention.

Figure 8:
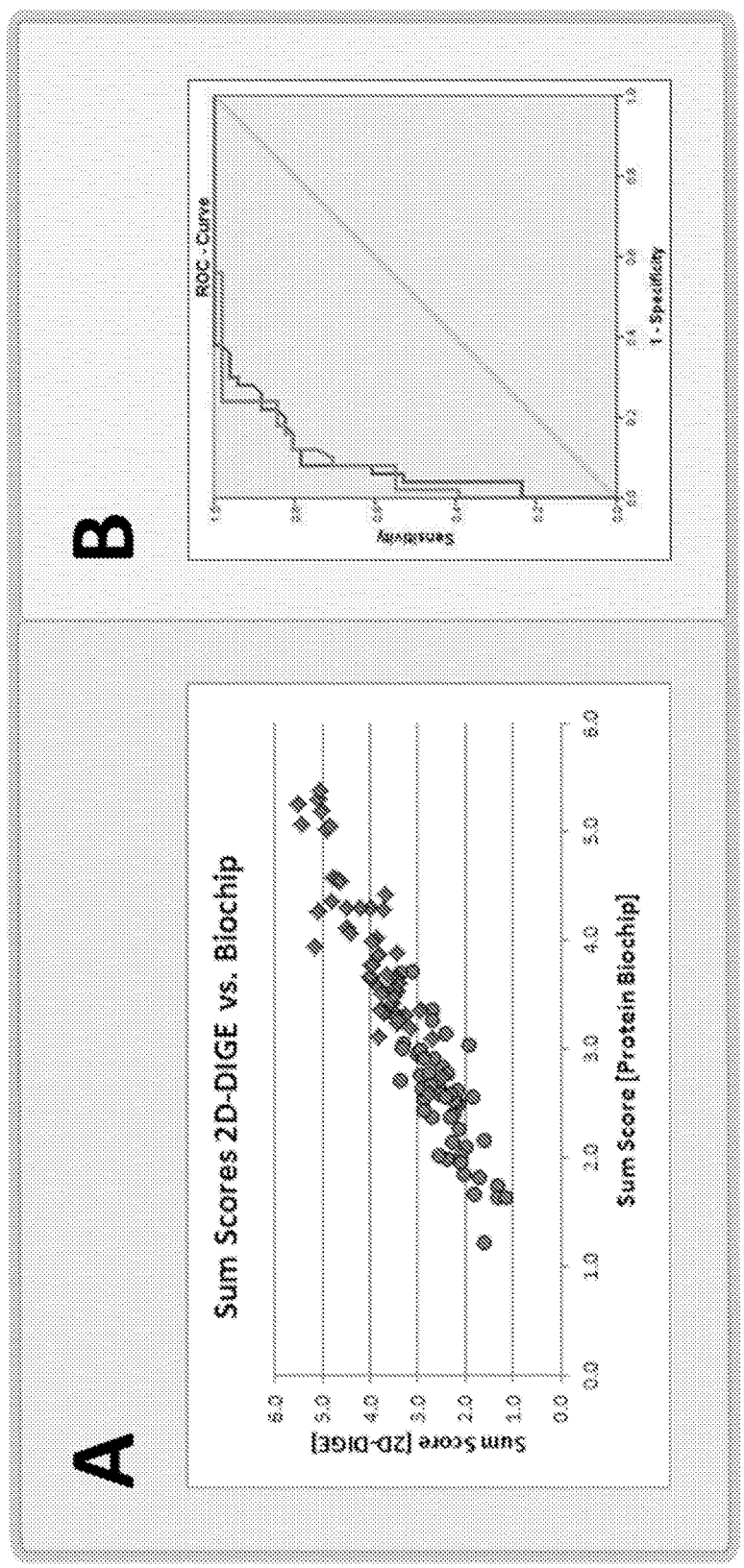
FIG. 8 shows statistical analysis of AD and control samples with either 2D-DIGE or the protein biochip of the invention.

As shown in FIG. 8, both techniques were found to have good separation power of AD-patients and controls. At an optimal biochip cutoff of 3.066, the specificity was 86.3% (seven false positives) and the sensitivity even 96.1% (two false negatives).

FIG. 8(A) shows the scatter blot of the sum scores (arbitrary units, n=102) calculated from the Mao-B and tropomyosin concentrations combined with the APOE ε4- and GSTO1-allele count of. For APOE ε4-negative subjects, 0.6*GSTO1*A140 alleles were added, whereas 0.9*GSTO1D140 alleles were combined with the APOE ε4 alleles. AD-patients and control samples could be separated with a high sensitivity (94.1%) and specificity (90.2%) with a set cutoff of 3.5. Protein Biochip sum scores are plotted on the x-axis, those of 2D-DIGE on the y-axis. Samples obtained from AD-patients are indicated as red squares, green circles represent control samples.

FIG. 8(B) shows the comparison of the sum score ROC curves calculated for the 102 clinical samples with the data measured with either of the two platforms. The AUC of 0.964 (2D-DIGE) and 0.955 (protein biochip) were identical and define the sensitivity and specificity of the analyses.

Example 3

The number of alleles of ApoE4 in a patient's genome can determined at the protein expression level, using an ApoE4-specific antibody and, optionally, a panApoE antibody. The data presented in Table 8 show that at a measured concentration of >19.1 ng/ml, use of an ApoE4 antibody gives 100% sensitivity and specificity for determining the presence of 1 or 2 ApoE4 alleles. The data presented in Table 9 show that the use of the ApoE4 to panApoE4 ratio completely discriminates 0, 1 and 2 allele genomes. It is therefore preferably to use antibodies directed against both ApoE4 and panApoE and to calculate the ApoE4: panApoE4 ratio, in order to determine a patient's ApoE4 allele genotype at the protein level.

TABLE 8

| | | ApoE | |
|---|---|---|---|
| Sample | ApoE4 | ApoE4 Av. conc. [ng/ml] | panApoE Av. conc. [ng/ml] |
| A167 | 2 | 600.5 | 307.1 |
| A44 | 2 | 473.4 | 172.0 |
| A41 | 2 | 463.5 | 165.3 |
| A43 | 2 | 452.9 | 157.3 |
| A183 | 2 | 418.3 | 209.1 |
| A123 | 2 | 397.2 | 415.8 |
| A34 | 2 | 368.3 | 140.7 |
| A36 | 2 | 359.6 | 134.3 |
| A63 | 2 | 352.3 | 116.8 |
| A81 | 2 | 334.1 | 94.5 |
| A59 | 1 | 301.7 | 546.9 |
| A49 | 1 | 270.5 | 770.9 |
| A62 | 1 | 243.5 | 634.2 |
| A163 | 2 | 208.1 | 90.0 |
| A38 | 1 | 201.5 | 908.7 |
| A111 | 1 | 199.7 | 1496.1 |
| A39 | 1 | 196.5 | 633.6 |
| A40 | 1 | 194.9 | 477.7 |
| A33 | 1 | 194.1 | 1041.4 |
| K147 | 1 | 187.8 | 546.4 |
| A166 | 1 | 176.3 | 513.9 |
| A179 | 1 | 176.1 | 601.8 |
| A192 | 1 | 175.1 | 1105.3 |
| A65 | 1 | 174.8 | 765.6 |
| K216 | 1 | 162.0 | 416.9 |
| A30 | 1 | 161.0 | 1234.4 |
| A159 | 1 | 158.1 | 1797.0 |
| A155 | 1 | 151.3 | 868.2 |

TABLE 8-continued

| | | ApoE | |
|---|---|---|---|
| Sample | ApoE4 | ApoE4 Av. conc. [ng/ml] | panApoE Av. conc. [ng/ml] |
| A187 | 1 | 148.9 | 656.8 |
| A114 | 1 | 141.5 | 1463.6 |
| A64 | 1 | 138.4 | 537.6 |
| K334 | 1 | 138.2 | 357.6 |
| K257 | 1 | 136.9 | 1749.3 |
| A174 | 1 | 128.3 | 622.9 |
| A76 | 1 | 128.0 | 1737.5 |
| K149 | 1 | 126.7 | 1575.0 |
| A148 | 1 | 115.6 | 758.6 |
| A138 | 1 | 108.1 | 1010.2 |
| A72 | 1 | 107.7 | 1337.6 |
| K172 | 1 | 102.1 | 945.9 |
| A175 | 1 | 95.1 | 589.0 |
| K354 | 0 | 19.1 | 1317.6 |
| K364 | 0 | 18.4 | 3600.4 |
| K339 | 0 | 13.9 | 3314.7 |
| K351 | 0 | 12.6 | 1167.4 |
| A095 | 0 | 12.0 | 2185.4 |
| K206 | 0 | 11.9 | 2770.0 |
| A32 | 0 | 11.8 | 1428.1 |
| K299 | 0 | 11.8 | 3175.4 |
| A61 | 0 | 11.1 | 2107.5 |
| A134 | 0 | 11.1 | 2648.0 |
| K305 | 0 | 10.7 | 2867.8 |
| K337 | 0 | 10.7 | 1453.0 |
| K332 | 0 | 10.6 | 3163.0 |
| K329 | 0 | 10.4 | 1261.8 |
| A52 | 0 | 9.9 | 888.4 |
| K154 | 0 | 9.8 | 1426.6 |
| A37 | 0 | 9.8 | 1355.6 |
| A184 | 0 | 9.3 | 1195.3 |
| K148 | 0 | 9.2 | 1450.0 |
| K349 | 0 | 9.1 | 2583.3 |
| K150 | 0 | 9.0 | 1152.9 |
| K348 | 0 | 8.9 | 2547.9 |
| K324 | 0 | 8.6 | 1087.1 |
| A77 | 0 | 8.6 | 2297.3 |
| K320 | 0 | 8.5 | 2193.0 |
| A55 | 0 | 8.1 | 1419.4 |
| A199 | 0 | 8.1 | 2302.9 |
| K177 | 0 | 8.1 | 1414.1 |
| K361 | 0 | 7.9 | 2994.6 |
| K293 | 0 | 7.9 | 4233.8 |
| K245 | 0 | 7.7 | 3011.1 |
| A66 | 0 | 7.5 | 1593.5 |
| A42 | 0 | 7.2 | 1259.2 |
| K155 | 0 | 7.1 | 849.1 |
| K230 | 0 | 6.9 | 2302.9 |
| K159 | 0 | 6.8 | 1687.8 |
| K143 | 0 | 6.6 | 1120.6 |
| A31 | 0 | 6.6 | 1598.2 |
| K211 | 0 | 6.3 | 2542.8 |
| A80 | 0 | 6.3 | 1363.1 |
| K185 | 0 | 6.2 | 1123.3 |
| K158 | 0 | 6.1 | 1098.9 |
| K162 | 0 | 6.0 | 1464.8 |
| A74 | 0 | 5.9 | 4579.3 |
| K157 | 0 | 5.8 | 885.9 |
| K214 | 0 | 5.7 | 992.3 |
| K153 | 0 | 5.7 | 1169.3 |
| K221 | 0 | 5.2 | 668.6 |
| K217 | 0 | 5.2 | 1300.5 |
| K223 | 0 | 5.0 | 1188.5 |
| K213 | 0 | 4.9 | 2192.8 |
| A82 | 0 | 3.4 | 1053.4 |
| K219 | 0 | 3.2 | 772.5 |
| K184 | 0 | 3.1 | 1020.2 |
| K146 | 0 | 2.8 | 784.6 |
| K166 | 0 | 2.3 | 535.6 |
| K139 | 0 | 2.2 | 805.1 |
| K152 | 0 | 1.4 | 860.6 |
| K212 | 0 | 1.4 | 1432.4 |
| K215 | 0 | 1.3 | 733.9 |

TABLE 9

| Sample | ApoE4 | ApoE4 Av. conc. [ng/ml] | panApoE Av. conc. [ng/ml] | ApoE4/ panApoE |
|---|---|---|---|---|
| A81 | 2 | 334.1 | 94.5 | 3.54 |
| A63 | 2 | 352.3 | 116.8 | 3.02 |
| A43 | 2 | 452.9 | 157.3 | 2.88 |
| A41 | 2 | 463.5 | 165.3 | 2.80 |
| A44 | 2 | 473.4 | 172.0 | 2.75 |
| A36 | 2 | 359.6 | 134.3 | 2.68 |
| A34 | 2 | 368.3 | 140.7 | 2.62 |
| A163 | 2 | 208.1 | 90.0 | 2.31 |
| A183 | 2 | 418.3 | 209.1 | 2.00 |
| A167 | 2 | 600.5 | 307.1 | 1.96 |
| A123 | 2 | 397.2 | 415.8 | 0.96 |
| A59 | 1 | 301.7 | 546.9 | 0.55 |
| A40 | 1 | 194.9 | 477.7 | 0.41 |
| K216 | 1 | 162.0 | 416.9 | 0.39 |
| K334 | 1 | 138.2 | 357.6 | 0.39 |
| A62 | 1 | 243.5 | 634.2 | 0.38 |
| A49 | 1 | 270.5 | 770.9 | 0.35 |
| K147 | 1 | 187.8 | 546.4 | 0.34 |
| A166 | 1 | 176.3 | 513.9 | 0.34 |
| A39 | 1 | 196.5 | 633.6 | 0.31 |
| A179 | 1 | 176.1 | 601.8 | 0.29 |
| A64 | 1 | 138.4 | 537.6 | 0.26 |
| A65 | 1 | 174.8 | 765.6 | 0.23 |
| A187 | 1 | 148.9 | 656.8 | 0.23 |
| A38 | 1 | 201.5 | 908.7 | 0.22 |
| A174 | 1 | 128.3 | 622.9 | 0.21 |
| A33 | 1 | 194.1 | 1041.4 | 0.19 |
| A155 | 1 | 151.3 | 868.2 | 0.17 |
| A175 | 1 | 95.1 | 589.0 | 0.16 |
| A192 | 1 | 175.1 | 1105.3 | 0.16 |
| A148 | 1 | 115.6 | 758.6 | 0.15 |
| A111 | 1 | 199.7 | 1496.1 | 0.13 |
| A30 | 1 | 161.0 | 1234.4 | 0.13 |
| K172 | 1 | 102.1 | 945.9 | 0.11 |
| A138 | 1 | 108.1 | 1010.2 | 0.11 |
| A114 | 1 | 141.5 | 1463.6 | 0.10 |
| A159 | 1 | 158.1 | 1797.0 | 0.09 |
| A72 | 1 | 107.7 | 1337.6 | 0.08 |
| K149 | 1 | 126.7 | 1575.0 | 0.08 |
| K257 | 1 | 136.9 | 1749.3 | 0.08 |
| A76 | 1 | 128.0 | 1737.5 | 0.07 |
| K354 | 0 | 19.1 | 1317.6 | 0.01 |
| A52 | 0 | 9.9 | 888.4 | 0.01 |
| K351 | 0 | 12.6 | 1167.4 | 0.01 |
| K155 | 0 | 7.1 | 849.1 | 0.01 |
| A32 | 0 | 11.8 | 1428.1 | 0.01 |
| K329 | 0 | 10.4 | 1261.8 | 0.01 |
| K324 | 0 | 8.6 | 1087.1 | 0.01 |
| K150 | 0 | 9.0 | 1152.9 | 0.01 |
| A184 | 0 | 9.3 | 1195.3 | 0.01 |
| K221 | 0 | 5.2 | 668.6 | 0.01 |
| K337 | 0 | 10.7 | 1453.0 | 0.01 |
| A37 | 0 | 9.8 | 1355.6 | 0.01 |
| K154 | 0 | 9.8 | 1426.6 | 0.01 |
| K157 | 0 | 5.8 | 885.9 | 0.01 |
| K148 | 0 | 9.2 | 1450.0 | 0.01 |
| K143 | 0 | 6.6 | 1120.6 | 0.01 |
| K214 | 0 | 5.7 | 992.3 | 0.01 |
| A42 | 0 | 7.2 | 1259.2 | 0.01 |
| K177 | 0 | 8.1 | 1414.1 | 0.01 |
| A55 | 0 | 8.1 | 1419.4 | 0.01 |
| K158 | 0 | 6.1 | 1098.9 | 0.01 |
| K185 | 0 | 6.2 | 1123.3 | 0.01 |
| A095 | 0 | 12.0 | 2185.4 | 0.01 |
| A61 | 0 | 11.1 | 2107.5 | 0.01 |
| K364 | 0 | 18.4 | 3600.4 | 0.01 |
| K153 | 0 | 5.7 | 1169.3 | 0.00 |
| A66 | 0 | 7.5 | 1593.5 | 0.00 |
| A80 | 0 | 6.3 | 1363.1 | 0.00 |
| K206 | 0 | 11.9 | 2770.0 | 0.00 |
| K166 | 0 | 2.3 | 535.6 | 0.00 |
| A134 | 0 | 11.1 | 2648.0 | 0.00 |
| K223 | 0 | 5.0 | 1188.5 | 0.00 |
| K219 | 0 | 3.2 | 772.5 | 0.00 |
| K339 | 0 | 13.9 | 3314.7 | 0.00 |
| A31 | 0 | 6.6 | 1598.2 | 0.00 |
| K162 | 0 | 6.0 | 1464.8 | 0.00 |
| K159 | 0 | 6.8 | 1687.8 | 0.00 |
| K217 | 0 | 5.2 | 1300.5 | 0.00 |
| K320 | 0 | 8.5 | 2193.0 | 0.00 |
| A77 | 0 | 8.6 | 2297.3 | 0.00 |
| K305 | 0 | 10.7 | 2867.8 | 0.00 |
| K299 | 0 | 11.8 | 3175.4 | 0.00 |
| K146 | 0 | 2.8 | 784.6 | 0.00 |
| K349 | 0 | 9.1 | 2583.3 | 0.00 |
| K348 | 0 | 8.9 | 2547.9 | 0.00 |
| A199 | 0 | 8.1 | 2302.9 | 0.00 |
| K332 | 0 | 10.6 | 3163.0 | 0.00 |
| A82 | 0 | 3.4 | 1053.4 | 0.00 |
| K184 | 0 | 3.1 | 1020.2 | 0.00 |
| K230 | 0 | 6.9 | 2302.9 | 0.00 |
| K139 | 0 | 2.2 | 805.1 | 0.00 |
| K361 | 0 | 7.9 | 2994.6 | 0.00 |
| K245 | 0 | 7.7 | 3011.1 | 0.00 |
| K211 | 0 | 6.3 | 2542.8 | 0.00 |
| K213 | 0 | 4.9 | 2192.8 | 0.00 |
| K293 | 0 | 7.9 | 4233.8 | 0.00 |
| K215 | 0 | 1.3 | 733.9 | 0.00 |
| K152 | 0 | 1.4 | 860.6 | 0.00 |
| A74 | 0 | 5.9 | 4579.3 | 0.00 |
| K212 | 0 | 1.4 | 1432.4 | 0.00 |

The invention claimed is:

1. An ex vivo method for aiding the diagnosis of Alzheimer's disease in a patient comprising:
   (i) determining the number of alleles of apolipoprotein E4 (ApoE4) in the patient's genome using an ApoE4 specific monoclonal antibody that specifically binds an epitope containing residue 112 of ApoE4;
   (ii) determining the combined expression level of at least three platelet proteins in a platelet sample obtained from the patient,
   wherein the at least three platelet, proteins include at least one isoform of alpha-tropomyosin containing exon 1a and at least two platelet proteins selected from monoamine oxidase-B, coagulation factor XIIIa, wild-type glutathione S-transferase omega-1 (GSTO-1) or mutant GSTO-1 having an aspartic acid at position 140, wherein if there are no alleles of ApoE4 in the patient's genome then the expression level of wild-type GSTO-1 is determined in step (ii) and if there are one or two alleles of ApoE4 in the patient's genome then the expression level of mutant GSTO-1 is determined in step (ii), wherein the determining of part (ii) comprises contacting the platelet sample from the patient with a solid support comprising one or more antibodies that specifically bind to at least one isoform of alpha-tropomyosin containing exon 1a, and one or more ligands that specifically bind to at least two platelet proteins selected from monoamine oxidase-B, coagulation factor XIIIa, wild-type glutathione S-transferase omega-1 (GSTO-1) protein and/or mutant GSTO-1 protein immobilized thereon, and
   (iii) comparing the resulting value of step (ii) to a control value, wherein a result higher than the control value is indicative of Alzheimer's disease.

2. A method according to claim 1, wherein the at least one isoform of alpha-tropomyosin containing exon 1a is selected from one or more of S1855, S1827, S1896 and S1941.

3. A method according to claim 2, wherein the at least one isoform of alpha-tropomyosin is S1855.

4. A method according to claim 2, wherein the expression level of at least one isoform of alpha-tropomyosin containing exon 1a is calculated as the sum of the expression of each of the isoforms S1855, S1827, S1896 and S1941.

5. A method according to claim 1, wherein the expression level of monoamine oxidase-B is determined in step (ii) of claim 1.

6. A method according to claim 1, wherein step (ii) further comprises determining the expression level of ApoE4 protein and/or total ApoE protein in the platelet sample.

7. The method of claim 1, wherein the at least three antibodies that bind platelet proteins bind to alpha-tropomyosin isoform containing exon 1a, monoamine oxidase B (MAO-B) and wild-type glutathione S-transferase omega-1 (wtGSTO-1).

* * * * *

SEQUENCE LISTING

<160> NUMBER OF SEQ ID NOS: 2

<210> SEQ ID NO 1
<211> LENGTH: 20
<212> TYPE: PRT
<213> ORGANISM: Homo sapiens

<400> SEQUENCE: 1

Leu Asp Lys Glu Asn Ala Leu Asp Arg Ala Glu Gln Ala Glu Ala Asp
1               5                   10                  15

Lys Lys Ala Ala
            20

```
<210> SEQ ID NO 2
<211> LENGTH: 27
<212> TYPE: PRT
<213> ORGANISM: Homo sapiens

<400> SEQUENCE: 2

Glu Lys Val Ala His Ala Lys Glu Glu Asn Leu Ser Met His Gln Met
1               5                   10                  15

Leu Asp Gln Thr Leu Leu Glu Leu Asn Asn Met
            20                  25
```